United States Patent [19]

Su et al.

[11] Patent Number: 5,594,033
[45] Date of Patent: Jan. 14, 1997

[54] SECOAPORPHINE COMPOUND ON ARRHYTHMIA

[75] Inventors: Ming-Jai Su; Che-Ming Teng; Shoei-Sheng Lee, all of Taipei, Taiwan

[73] Assignee: National Science Council, Taipei, Taiwan

[21] Appl. No.: 186,521

[22] Filed: Jan. 26, 1994

[30] Foreign Application Priority Data

Aug. 13, 1993 [JP] Japan ..................... 5-201587

[51] Int. Cl.$^6$ .................. A61K 31/135; C07C 217/60
[52] U.S. Cl. .................. 514/654; 514/609; 564/105; 564/379
[58] Field of Search .................. 564/105, 379; 514/609, 654

[56] References Cited

PUBLICATIONS

Teng et al., Chemical Abstracts, vol. 121(1994) 73473h.
Lee et al. Chemical Abstracts, vol. 118 (1992) 39219.
Lu et al, Chemical Abstracts, vol. 105 (1989) 153373.
Gorecki et al, Chemical Abstracts, vol. 95 (1981) 203612.
Bremner et al, Chemical Abstracts, vol. 88 (1978) 19181.
Smissman et al, Chemical Abstracts, vol. 73 (1970) 82368.
T. Kametani et al., "Biogenetic Type Syntheses of Aporphine Alkaloids, Isoboldine and Glaucine", *Tetrahedron*, vol. 25, pp. 3667 to 3673, published prior to or on Dec. 31, 1969.

*Primary Examiner*—Richard L. Raymond
*Attorney, Agent, or Firm*—Bucknam and Archer

[57] ABSTRACT

Novel secoaporphine compounds having the formula I

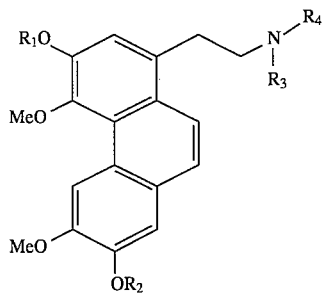

wherein a) $R_1$, $R_2$ and $R_3$, $R_4$ are each methyl group; or b) $R_1$, $R_2$, and $R_4$ are each methyl group; $R_3$ is benzyl, ethyl or allyl; or c) $R_1$, $R_2$, and $R_3$ are each hydrogen, $R_4$ is methyl; or d) $R_1$ and $R_2$ are each hydrogen, $R_3$ is benzyl, $R_4$ is methyl; or e) $R_1$ and $R_2$ are each hydrogen, $R_3$ is cyano, $R_4$ is methyl group, and a salt thereof with a pharmaceutically acceptable acid. The novel compounds are useful in the treatment of arrhythmia.

6 Claims, 12 Drawing Sheets

Fig.4A  Quinidine 3μM

Fig.4B  N-Allylsecoboldine 3μM

Fig.6A Control

Fig.6B N-Allylsecoboldine 0.6 μM

A·· ○ Control
B·· ● N-Allylsecoboldine 0.6 μM

*Fig.10A* Control

*Fig.10B* N-Allylsecoboldine 3μM

*Fig.10C* N-Allylsecoboldine 9μM

SECOAPORPHINE COMPOUND ON ARRHYTHMIA

BACKGROUND OF THE INVENTION

There are various types of human cardiovascular diseases with complicated etiology, among them hypertension, cardiac failure, angina pectoris and arrhythmia are usually encountered. Drugs used in the treatment of cardiac arrhythmia are generally classified into four groups, such as sodium channel blockers, adrenergic blocking agents, potassium channel blockers and calcium channel blockers. Other cardiovascular agents include nitrates, digitalis, anticoagulants, diuretics, and lipid-lowering agents . . . etc. Some patients are simultaneously attacked by at least two types of cardiovascular disease, for instance, patients who suffer from cardiac failure and arrhythmia should not be treated with calcium channel blockers or strong sodium channel blockers with calcium channel blocking activity such quinidine. Patients having both angina pectoris and atrial arrhythmia can be treated with calcium channel blockers which relieve the symptoms of angina pectoris by reducing the oxygen demand of myocardium.

Secoaporphine derivatives such as morphine, codeine are present in Papaveraceae or Sapindaceae plants. The secoaporphine structure is related to that of aminobenzylisoquinoline, which is synthesized in vivo via tyrosine-isoquinoline pathway. Aminobenzylisoquinoline can also be synthesized in the laboratory according to the method of Pachorr in the presence of sodium nitrate. Most secoaporphine derivatives, for instance morphine, codeine, apomorphine are used as narcotic or antiemetic drugs. Secoaporphine derivatives rarely have been reported to exhibit a pharmacological effect on the cardiovascular system.

SUMMARY OF THE INVENTION

This invention covers the synthesis of a series of secoaporphine derivatives of formula I wherein
a) $R_1$, $R_2$ and $R_3$, $R_4$ are each a methyl group; or b) $R_1$, $R_2$, and $R_4$ are each methyl group; and $R_3$ is benzyl, ethyl or allyl; or c) $R_1$, $R_2$, and $R_3$ are each hydrogen, and $R_4$ is methyl; or d) $R_1$ and $R_2$ are each hydrogen, $R_3$ is benzyl and $R_4$ is methyl; or e) $R_1$ and $R_2$ are each hydrogen, $R_3$ is cyano, $R_4$ is methyl, and a salt thereof with a pharmaceutically acceptable acid.

BRIEF DESCRIPTION OF THE DRAWINGS

FIG. 3 illustrates the influence of secoaporphine derivatives on the contractile force and the heart rate in rats. (A) N-allylsecoboldine (B) N-benzylsecoboldine (C) N-allylsecoglaucine (D) N-benzylsecoglaucine (E) N-allylsecopredicentrine FIG. 4 shows the effects on the action potential-prolongation of the myocyte action potential. (A) quinidine (B) N-allylsecoboldine FIG. 5 shows the effect of secoaporphine derivatives on transient outward current and steady-state outward current of the rat ventricular cell.

FIG. 6 shows the effect of N-allylsecoboldine on potential-dependent steady-state inactivation characteristic of transient outward current ($I_{to}$).

FIG. 7 illustrates the effect of N-allylsecoboldine on delayed outward potassium current in guinea pig ventricular cell.

FIG. 9 illustrates the effect of N-allylsecoboldine on $I_{Na}$ recovery from inactivation.

FIG. 10 illustrates the effect of N-allylsecoboldine on potential-dependent inactivation of $I_{Na}$.

FIG. 11 illustrates the actual degree of inhibition of calcium inward current by a secoaporphine derivation.

FIG. 12 shows the inhibition of secoaporphine derivatives on arrhythmia in guinea pig left atria induced by Ouabain (0.6 μM).

Figure 1:
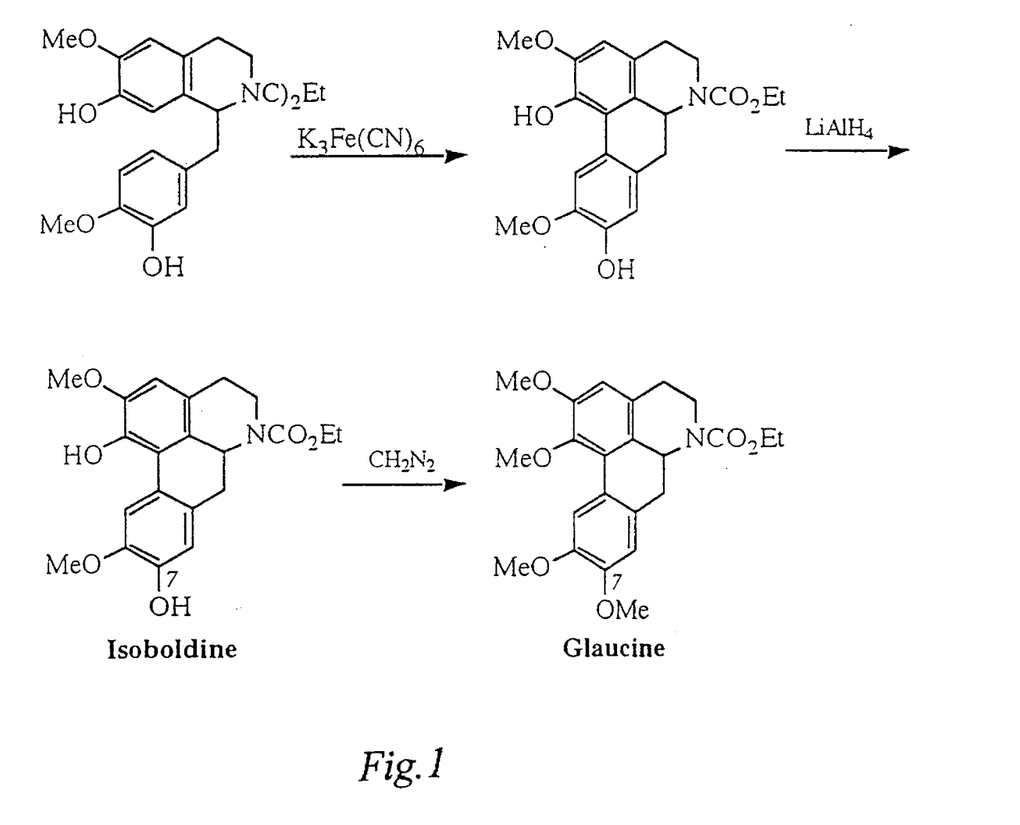
FIG. 1 shows the synthesis of secoaporphine derivatives using aminobenzylisoquinoline as the starting material.

The synthesis of secoaporphine derivatives was reported by T. Kametani et al (Tetrahedron, vol. 25, pp. 3667, 1969) using aminobenzylisoquinoline as the starting material (see FIG. 1). The process gives isoboldine and by reaction of the latter with diazomethane glaucine is produced.

Figure 2:
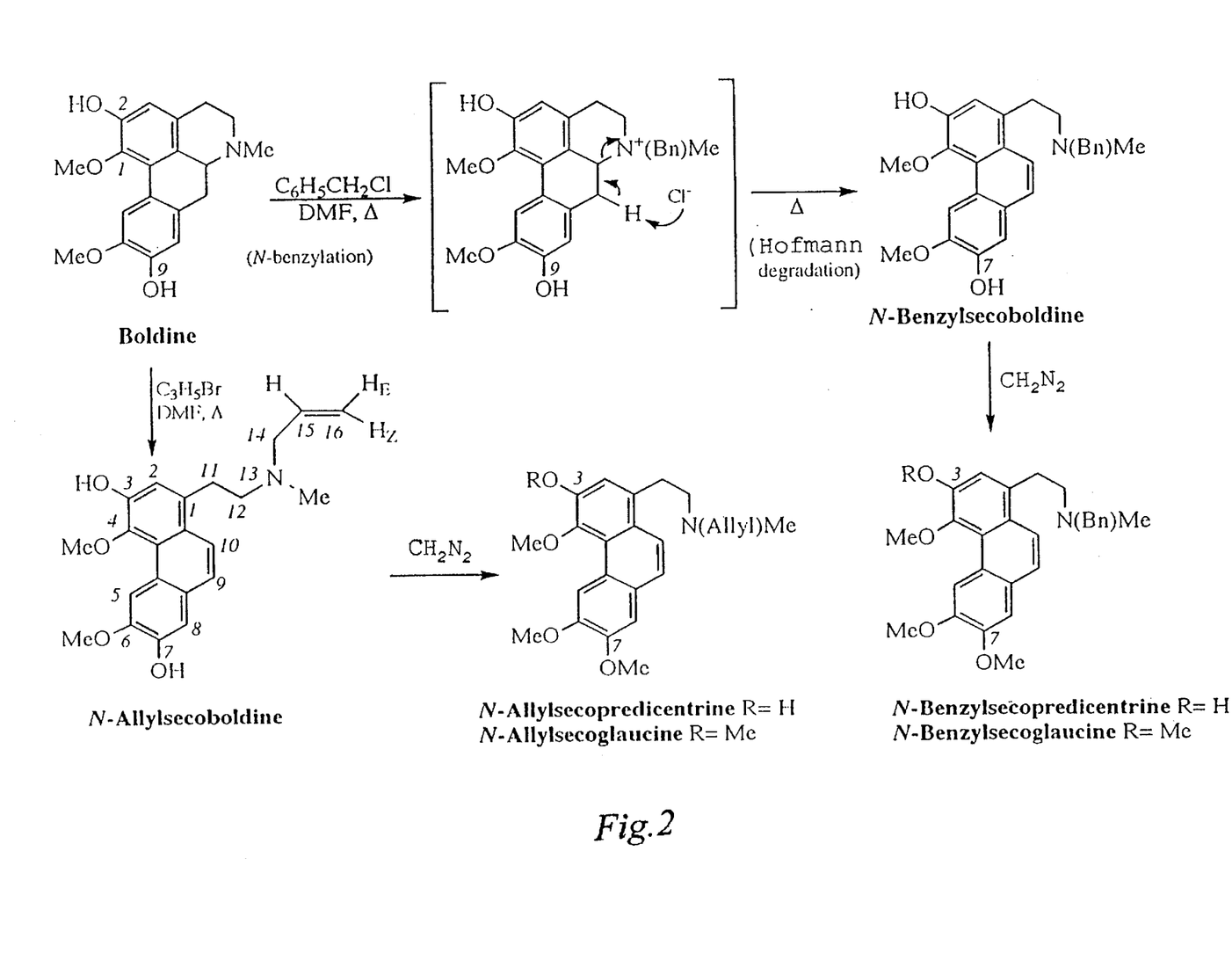
FIG. 2 shows the synthesis of the compounds according to the present invention.
Figure 3A:
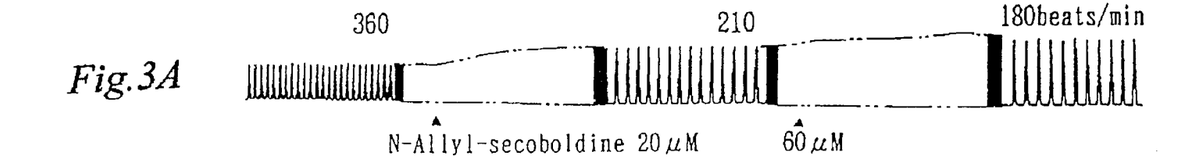
Figure 3B:
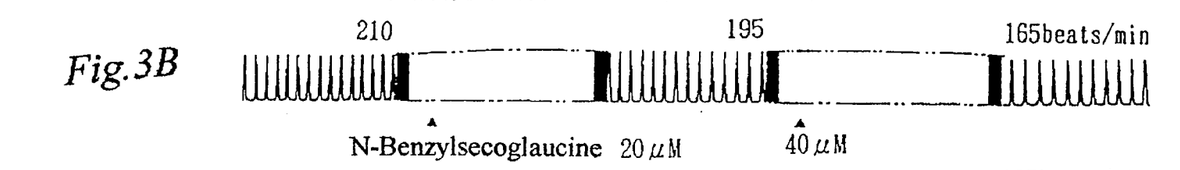
Figure 3C:
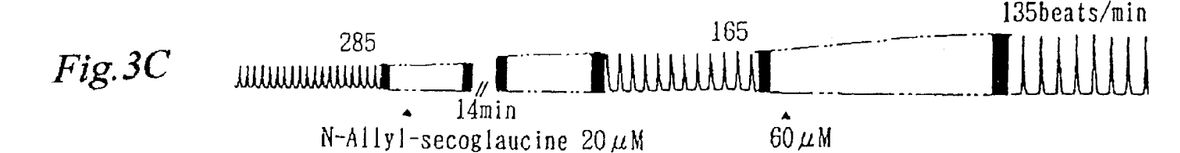
Figure 3D:
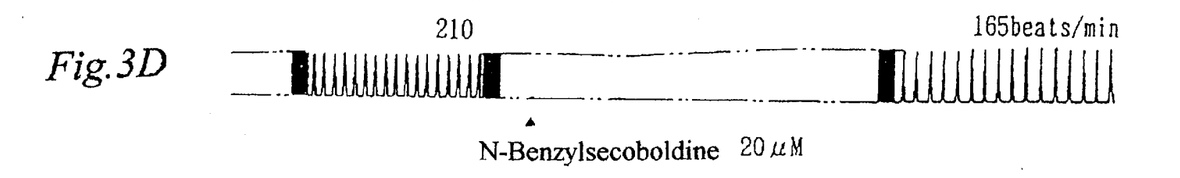
Figure 3E:
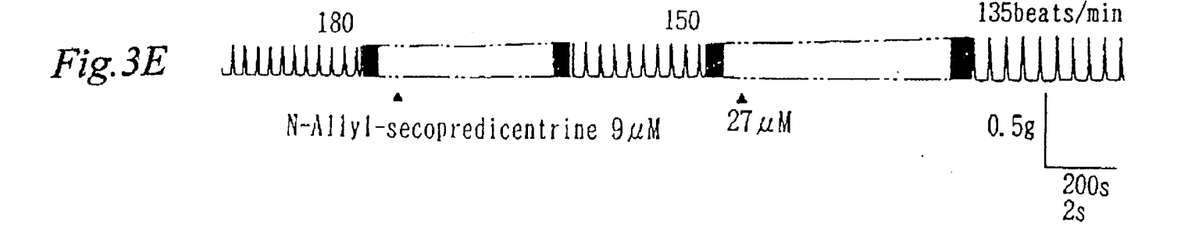

The novel compounds of formula I were prepared by the Hofmann reaction from the boldine 1,10-dimethoxyaporphine-2,9-diol, by reaction with $R'CH_2Cl$ of formula III (FIG. 2). The nitrogen ring of aporphine is open to give 1-substituted secoboldine, which is 1-substituted-4,6-dimethoxysecoaporphine-3,7-diol. In the compound of formula III $R'CH_2Cl$ $R_5$ is hydrogen, $C_{1-8}$ alkyl group, phenyl, cyano group, and $R'CH_2$ is allyl or benzyl. By methylation of the 1-substituted secoboldine with equimolar amounts of diazomethane the 1-substituted-7-methyl-secoboldine or 1-substituted-3,7-dimethyl-secoboldine are obtained—see FIG. 2.

The novel compounds of this invention are secoaporphine derivatives and have formula I wherein
$R_1$, $R_2$, $R_4$ is hydrogen, lower alkyl, $R_3$ is lower alkyl cyano; but a) $R_1$, $R_2$ and $R_3$, $R_4$ are each methyl group; or b) $R_1$, $R_2$ and $R_4$ are each methyl group; or $R_3$ is benzyl, ethyl or allyl; or c) $R_1$, $R_2$, and $R_3$ are each hydrogen, $R_4$ is methyl group; or d) $R_1$, and $R_2$ are each hydrogen, $R_3$ is benzyl and $R_4$ is methyl; or e) $R_1$ and $R_2$ are each hydrogen, $R_3$ is cyano, $R_4$ is methyl group.

Examples of the salts include inorganic and organic acid addition salts such as the hydrochloride, the hydrobromide, the sulphate, the phosphate, the acetate, the fumarate, the maleate, the citrate, the lactate, the tartrate, the oxalate, or other pharmaceutically acceptable inorganic and organic acid addition salts.

The synthetic method according to FIG. 2 was followed. Boldine was dissolved in excess N,N-dimethylformamide (DMF), and the Hofmann reaction was carried out. Methylation of the 1-substituted secoboldine with equimolar amounts diazomethane at a temperature of 4° C. for 24 hrs, was carried out. The precipitate was isolated on a silica gel column and purified. The products were analyzed for their carbon, hydrogen and nitrogen content. Melting points were measured in open capillary tubes with an electrothermometer. Infrared spectra were recorded on a Parkin-Elmer model 983G spectrometer. The $^1H$-NMR spectra were obtained on a Jeol FX-100 NMR spectrometer. Mass spectra were measured with a Jeol JMS-400 mass spectrometer.

The following novel secoaporphine compounds were synthesized:

TABLE 1

| Compound | $R_1$ | $R_2$ | $R_3$ | $R_4$ |
|---|---|---|---|---|
| (1) | H | H | allyl | Me |
| (2) | H | H | H | " |
| (3) | H | Me | allyl | " |
| (4) | Me | Me | allyl | " |
| (5) | H | H | benzyl | " |
| (6) | H | Me | benzyl | " |
| (7) | Me | Me | benzyl | " |
| (8) | Me | Me | Me | " |
| (9) | H | Me | Me | " |
| (10) | Me | H | Me | " |
| (11) | H | H | Et | " |
| (12) | H | Me | Et | " |
| (13) | Me | Me | Et | " |
| (14) | H | H | n-Butyl | " |
| (15) | Me | Me | n-Butyl | " |
| (16) | H | Me | n-Butyl | " |
| (17) | H | H | i-Butyl | " |
| (18) | H | Me | i-Butyl | " |
| (19) | Me | Me | i-Butyl | " |
| (20) | H | H | n-Hexyl | " |
| (21) | H | Me | n-Hexyl | " |
| (22) | Me | Me | n-Hexyl | " |
| (23) | H | H | n-Propyl | " |
| (24) | H | Me | n-Propyl | " |
| (25) | Me | Me | n-Propyl | " |
| (26) | H | H | CN | " |
| (27) | H | Me | CN | " |
| (28) | Me | Me | CN | " |

The effect of the compounds of formula I on heart contraction, heart rate, action potential, and membrane current was studied in rats. The antiarrhythmic effect of these compounds was indirectly evaluated by examining whether they inhibit the membrane sodium or potassium current or prolong the action potential of rat myocytes. Direct evaluation of the antiarrhythmic effect was conducted to determine whether these compounds exert inhibitory effect on arrhythmia in guinea pig atria induced by a toxic dose of the inotropic agent ouabain. The antiarrhythmic potency of each test compound was compared with that of a known antiarrhythmic drug such as lidocaine.

INFLUENCE OF SECOAPORPHINE DERIVATIVES ON THE CONTRACTILE FORCE AND THE HEART RATE IN RATS

Method:

After anesthetizing rats with pentobarbital, the heart was taken out, both the atrium and the right ventricle were separately placed in 10 ml of Tyrode solution. The spontaneous contraction of the right atrium was recorded. The contraction of the left atrium and the right ventricle was driven by stimulation at a frquency of twice per second.

TABLE 2

Compounds which alter the contraction force and the heart rate in rats

| | |
|---|---|
| compound 1 | N-allylsecoboldine |
| compound 3 | N-allylsecopredicentrine |
| compound 4 | N-allylsecoglaucine |
| compound 5 | N-benzylsecoboldine |
| compound 7 | N-benzylsecoglaucine |
| compound 8 | N-methylsecoglaucine |
| compound 9 | N-methylsecopredicentrine |
| compound 26 | N-cyanosecoboldine |

Results:

The compounds shown in FIG. 3 and Table 2 all caused bradycardia in the right atrium. However, the contractile force of the right atrium was increased. All test compounds at the concentration between 3 to 30 μM increased the contractile force of the electrically driven left atria and right ventricular preparations. The effect of the compound (9 μM) on the spontaneous beating rate of the right atrium and the induced contraction of the left atrium are summarized in Table 3.

TABLE 3

Inotropic and chronotropic action of N-allylsecoboldine on rat right atria, left atria and right ventricular strips contractions of left atria and right ventricular strips were driven by electrical stimulation at 2 Hz. Data (n = 6) is expressed as the mean ± S.E.M.

| | N-allylsecoboldine 9 μM | |
|---|---|---|
| preparations | Contractile tension (%) | H. R. (%) |
| right atria | 164 ± 14** | 58.5 ± 3.4** |
| left atria | 126.3 ± 6.3** | — |
| right ventricle | 126 ± 7.3* | — |

ELECTROPHYSIOLOGICAL STUDIES ON RAT AND GUINEA PIG MYOCYTES

Method:

Ventricular cells isolated from rats and guinea pigs were placed in a chamber mounted on an inverted microscope, the effects of the test compounds on the action potential and the membrane current were studied by single cell current clamp and voltage clamp technique.

Figure 4A:
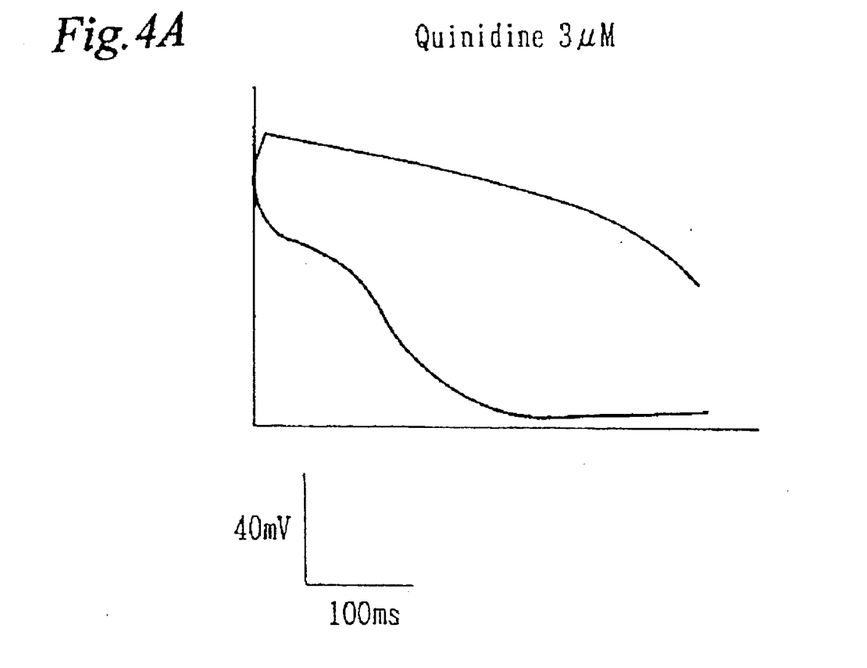
Figure 4B:
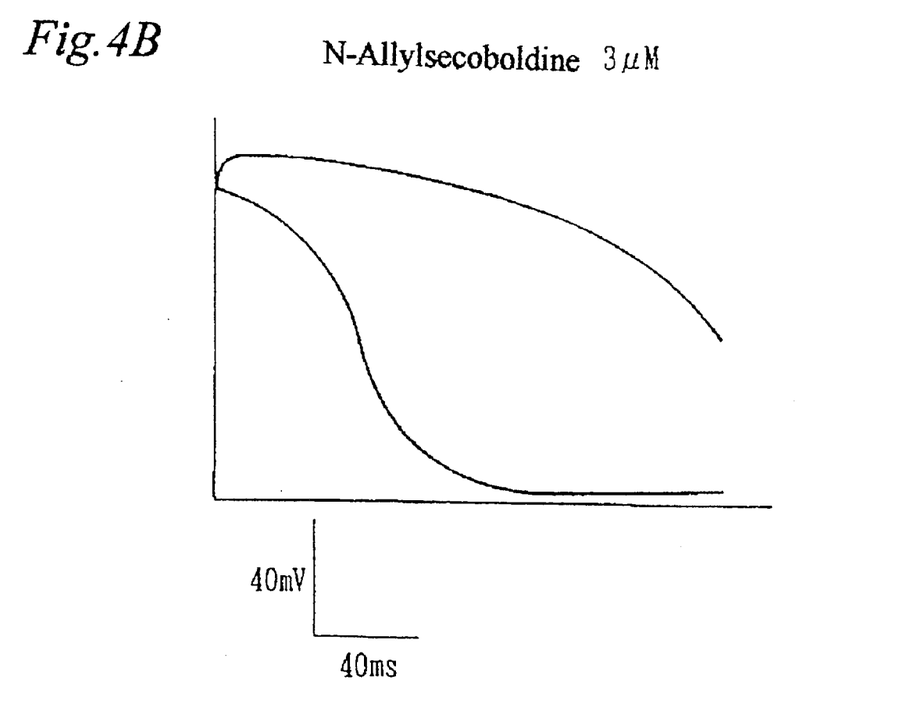

Results:

Effects on the action potential-prolongation of the myocyte action potential was seen at 1 μM of N-allylsecoboldine, and the duration of the action potential driven at 0.2 Hz was prolonged to five fold when cell were treated with 3 μM of this compound. The inhibition of the rate of depolarization of the action potential of N-allylsecoboldine was similar to that of quinidine, except that 30 MM quinidine decreased action potential plateau, whereas N-allylsecoboldine increased it. This is shown in FIG. 4. Other derivatives of formula I such as N-allylsecoglaucine (compound 4) caused a very similar effect on the myocyte action potential as N-allylsecoboldine.

Figure 5A:
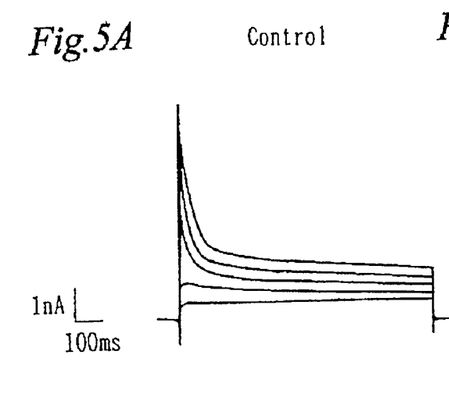
FIG. 5A and FIG. 5B are typical current traces obtained in control and in the presence of 3 μM N-benzylsecoboldine.
Figure 5B:
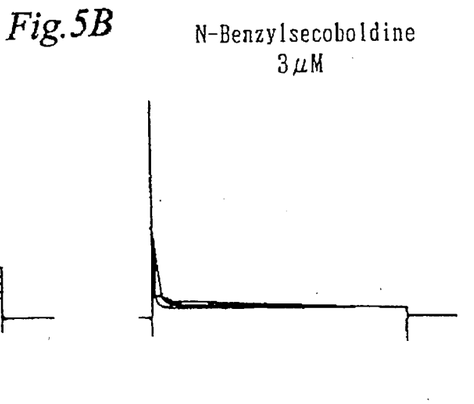
Figure 5C:
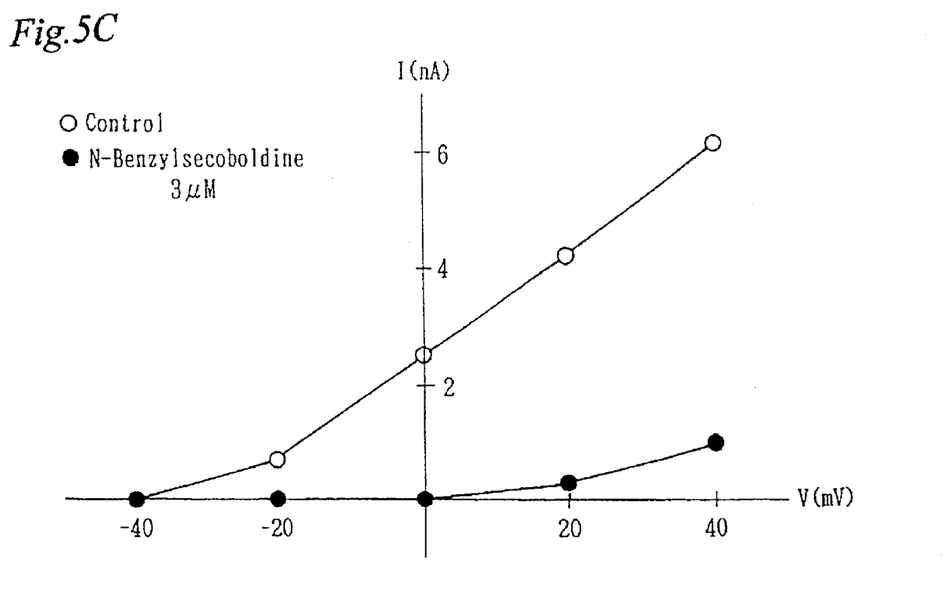
FIG. 5C shows curves of transient outward current in control (○) and in the presence of 3 μM N-benzylsecoboldine (●).
Figure 6A:
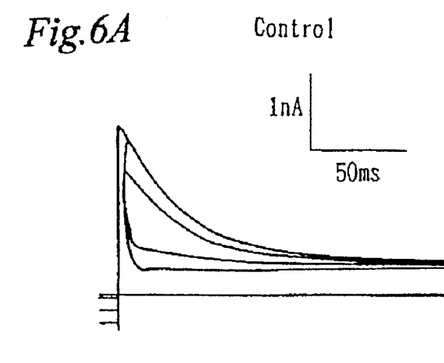
FIG. 6A and FIG. 6B show typical outward currents elicited by depolarization pulse to 0 mV from different holding potentials obtained in control and in the presence of 0.6 μM N-allylsecoboldine.
Figure 6B:
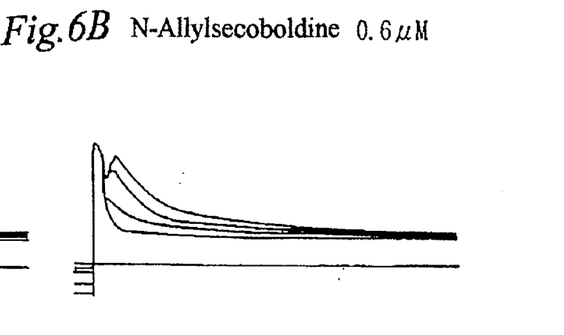
Figure 6C:
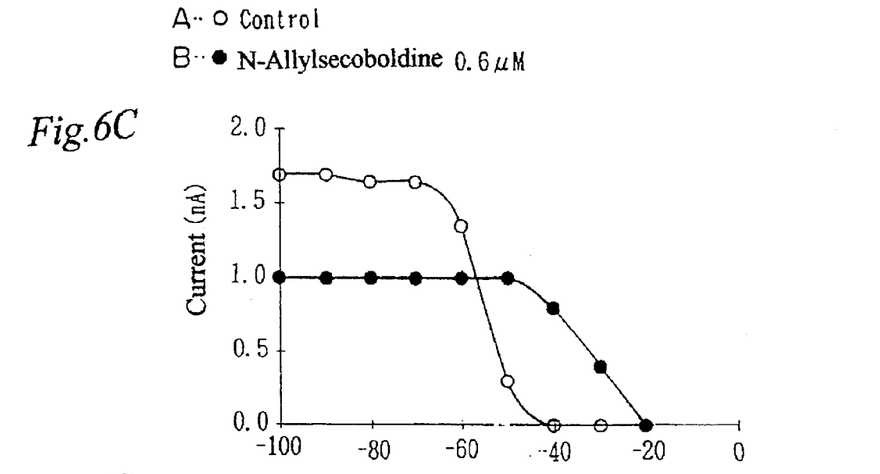
FIG. 6C illustrates potential-dependent inactivation curves of $I_{to}$ in control (○) and in the presence of 0.6 μM N-allylsecoboldine.
Figure 6D:
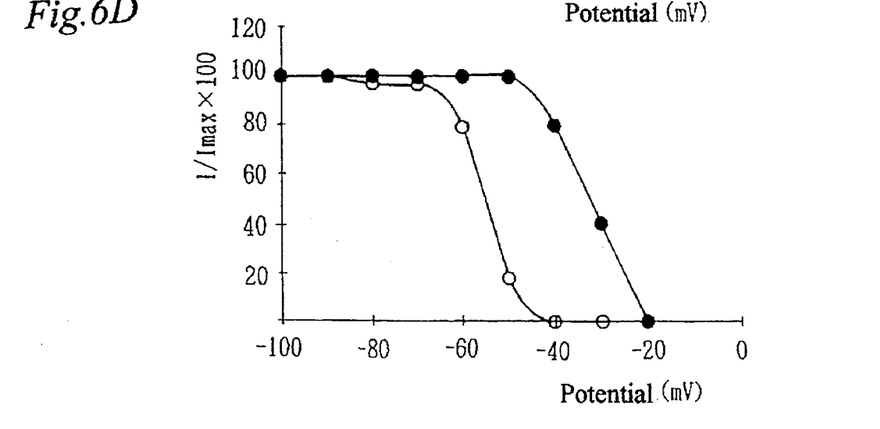
FIG. 6D illustrates norniolized potential-dependent inactivation curve of $I_{to}$ in control (○) and in the presence of N-allylsecoboldine.
Figures 7A, 7B:
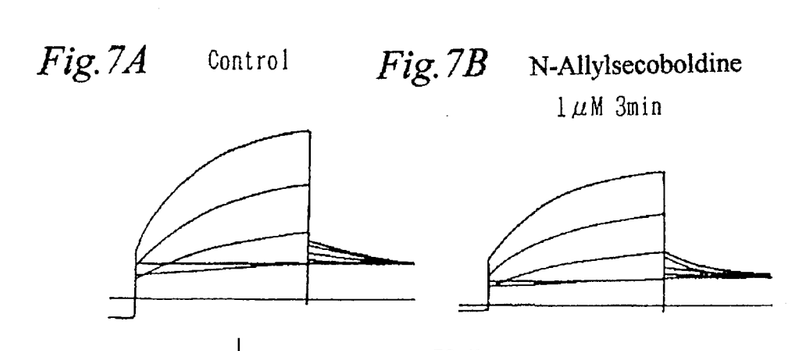
FIGS. 7A–7D illustrate the effect of N-allylsecoboldine on delayed outward potassium current in guinea pig ventricular cell. Typical outward current traces obtained in control and in the presence of 1 μM, 3 μM and 9 μM N-allysecoboldine.
Figure 7C:
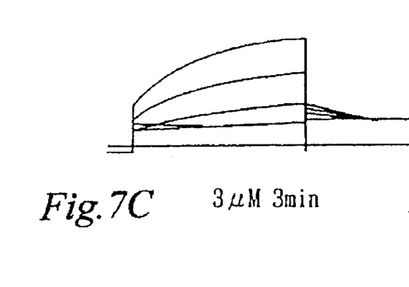
Figure 7D:
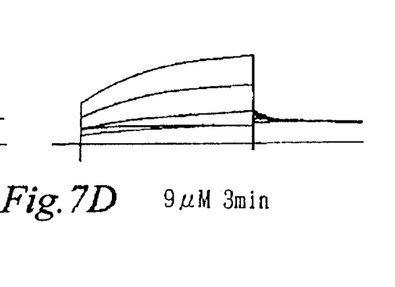
Figure 7E:
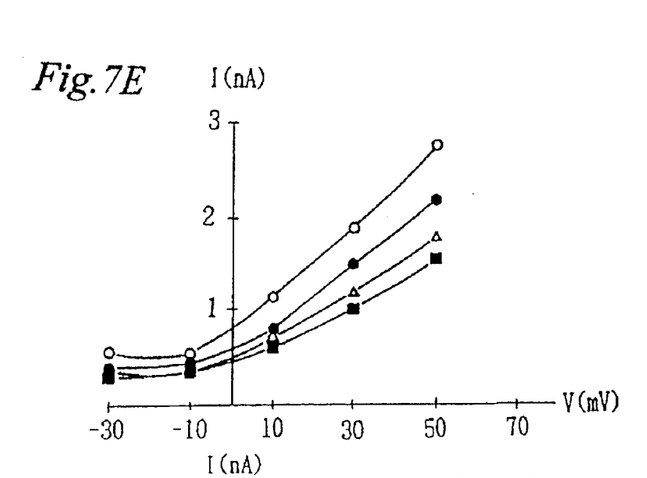
FIGS. 7E and 7F show curves for delayed outward current in control (○) and in the presence of 1 μM (●), 3 μM (Δ) and 9 μM (■) N-allylsecoboldine.
Figure 7F:
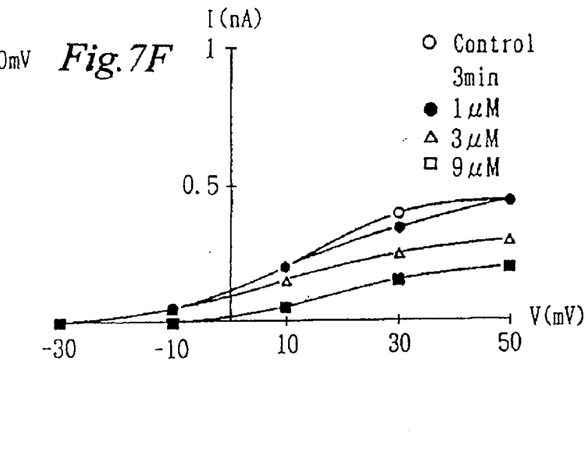

Effects on potassium current-3 μM of N-benzylsecoboldine (compound 5) had a more profound inhibitory effect on transient outward current (Ito) in rat ventricular cell than quinidine. Quinidine reduced about 60% of Ito at the same concentration as shown in FIG. 5. Other derivatives were also able to decrease Ito, for instance, 0.6 μM N-allylsecoboldine (compound 1) reduced 40 to 50% of Ito as shown in Table 4.

TABLE 4

| Compound | Concentration | Ito |
|---|---|---|
| compound 26 N-cyanosecoboldine | 6 μm | −80% |
| compound 9 N-methyl-secopredicentrine | 6 μm | −60% |
| compound 8 N-methyl-secoglaucine compound 3 N-allylsecopredicentrine | 6 μm | −70% |

Figures 8A, 8B:
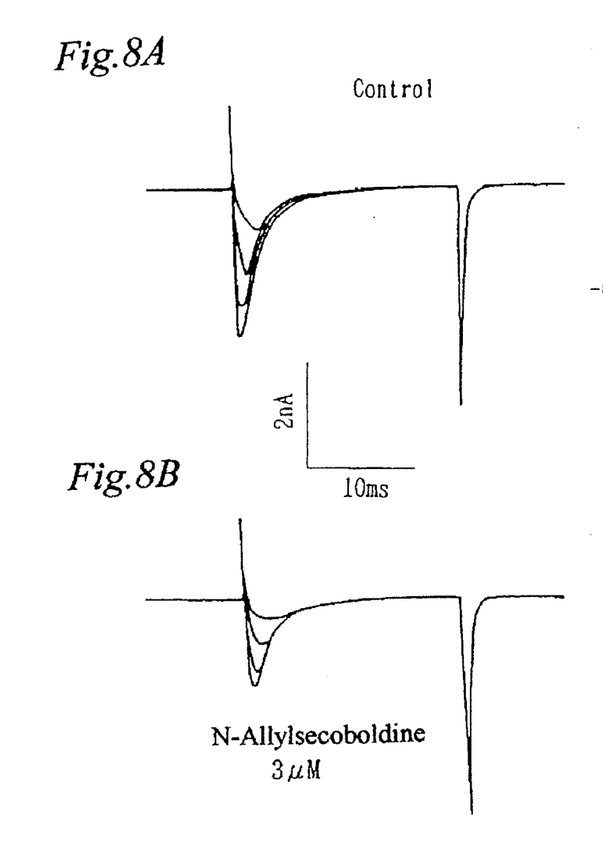
FIG. 8A and FIG. 8B illustrate the effect of N-allylsecoboldine on sodium inward current of rat ventricular cell and specifically typical current traces elicited by depolarizations obtained in control and in the presence of 3 μM N-allylsecoboldine.
Figure 8C:
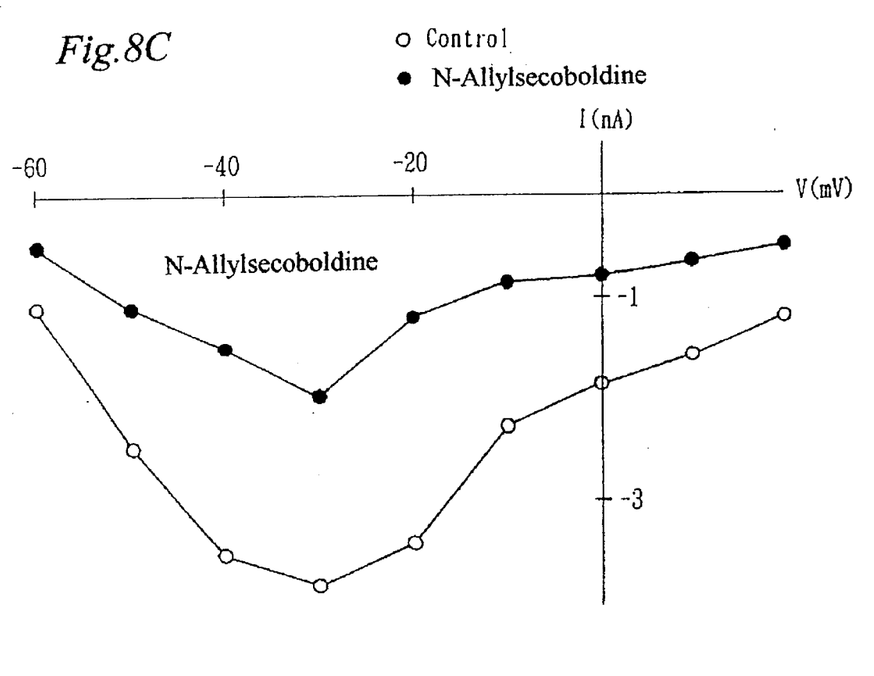
FIG. 8C shows curves of $I_{Na}$ in control (○) and in the presence of N-allylsecoboldine (●).

Although N-allylsecoboldine, compound 1, inhibited Ito, it shifted the potential-dependent inactivation curve of Ito to the right—see FIG. 6. This result indicates that N-allylsecoboldine does not enhance the inactivation of Ito. The N-allylsecoboldine not only inhibits Ito in rat ventricular cell but also inhibits delayed rectifier(IK) in guinea pig ventricular cell. This is shown in FIG. 7. The degree of inhibition of IK in guinea pig ventricle cell was 20 to 30% at 1 μM, 50–60% at 3 μM, 70–80% at 9 μM. N-benzylsecoboldine (compound 5) at 1 μM also caused a 30% inhibition of IK in guinea pig ventricular cell. The effects on sodium current in guinea pig atrial cell or rat ventricle cell were reduced to 25% of control by 0.9 to 1.2 μM of N-allylsecoboldine as shown in FIG. 8.

Figure 9A:
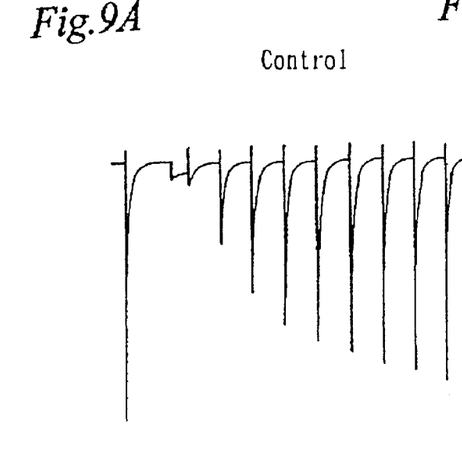
FIG. 9A shows typical current traces obtained in control.
Figure 9B:
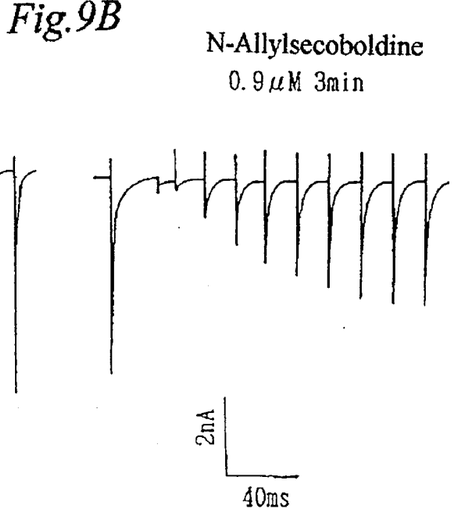
FIG. 9B shows typical current traces obtained in the presence of 0.9 μM N-allylsecoboldine.
Figure 9C:
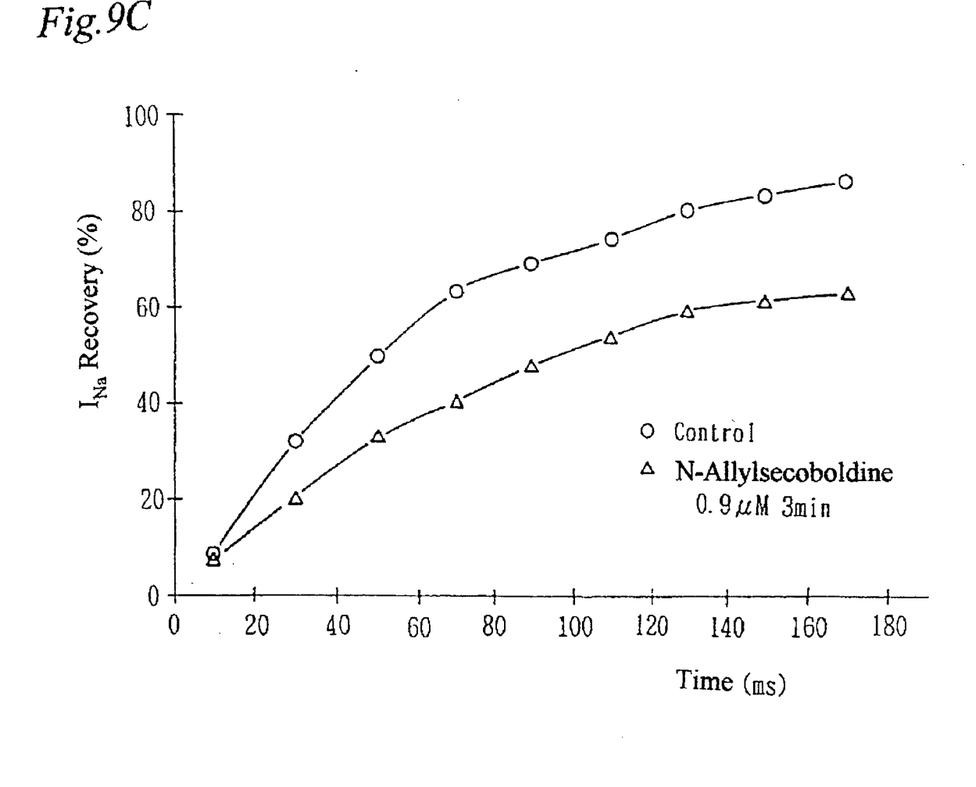
FIG. 9C shows the fractional recovery of $I_{Na}$ plotted against the time intervals after repolarization to −80 mV in control (○) and in the presence of of 0.9 uM N-allylsecoboldine (Δ).
Figure 10A:
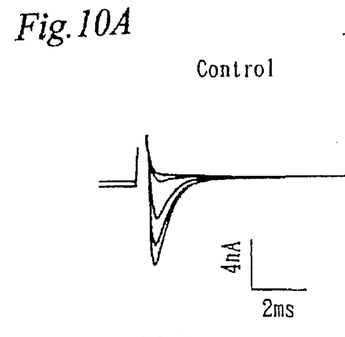
FIGS. 10A, 10B and 10C are typical current traces obtained in control and in the presence of 3 μM and 9 μM N-allylsecoboldine.
Figure 10B:
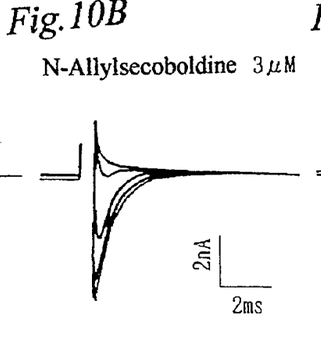
Figure 10C:
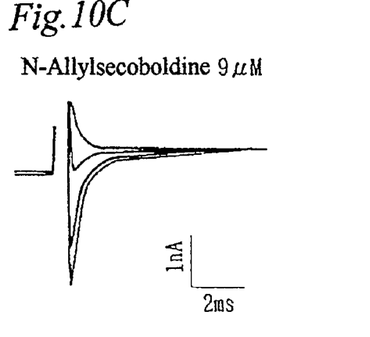
Figure 10D:
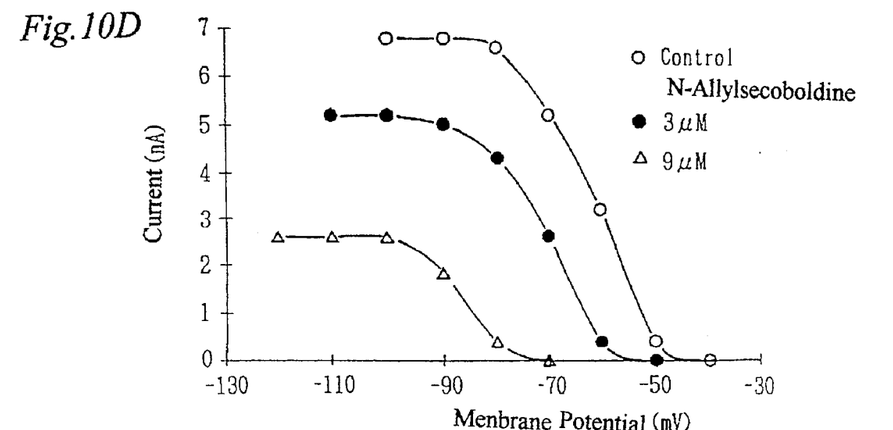
FIG. 10D shows the potential-dependent inactivation curve (○) and in the presence of 3 μM (■) and 9 μM (Δ) N-allylsecoboldine.
Figure 10E:
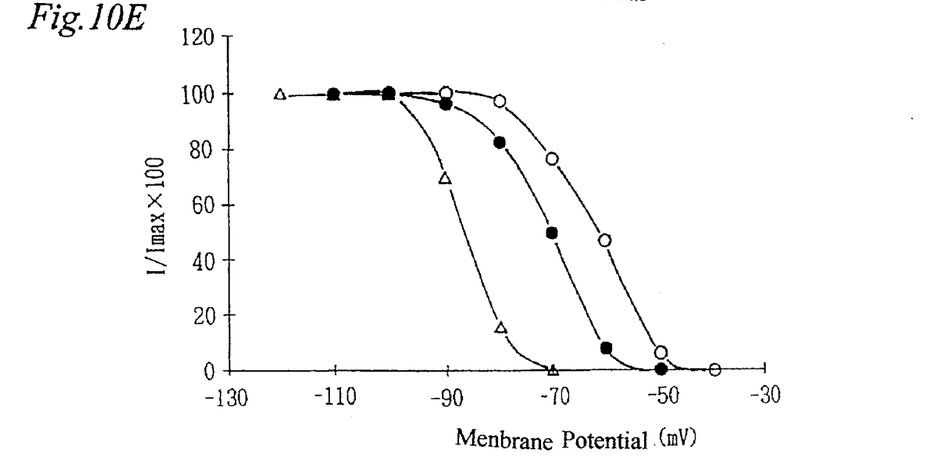
FIG. 10E illustrates the normalized potential-dependent inactivation curves of $I_{Na}$ in control (○) and in the presence of 3 μM (■) and (Δ) 9 μM N-allylsecoboldine.
Figure 11A:
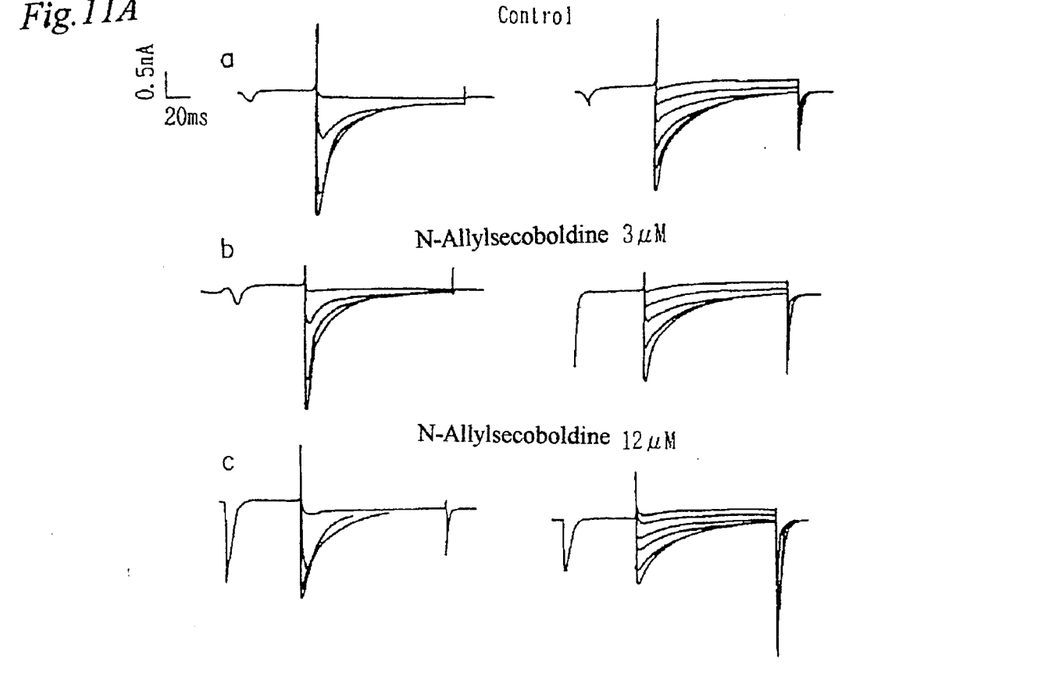
FIG. 11A illustrates typical calcium current records in control (a) and in the presence of 3 μM (b) and 12 uM (c) N-allylsecoboldine.
Figure 11B:
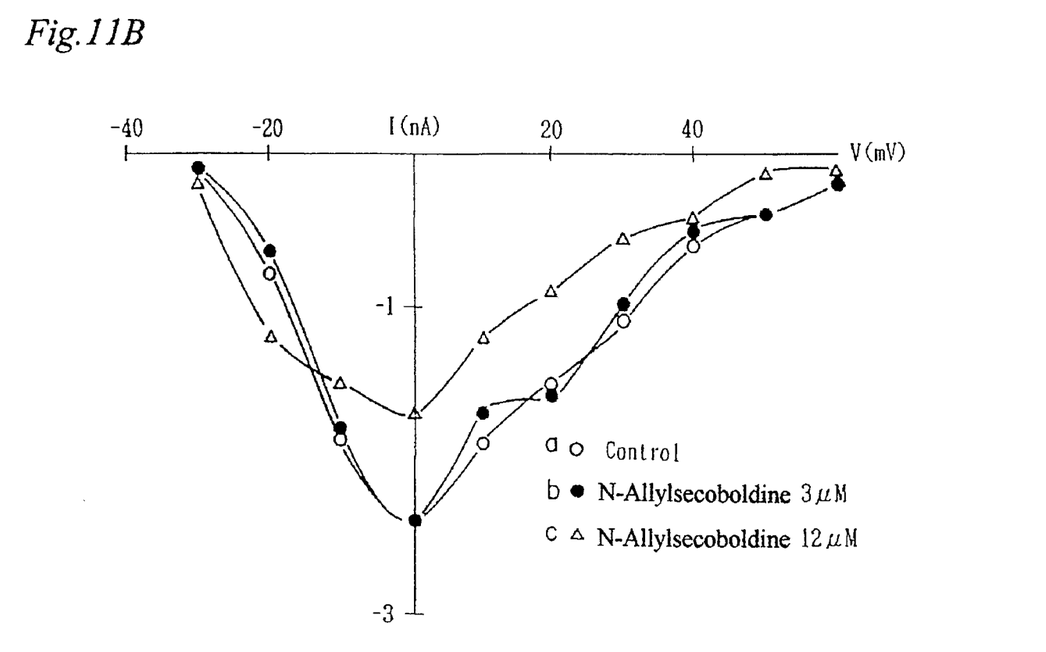
FIG. 11B shows curves of $I_{Ca}$ in control (○) and in the presence of 3 μM (●) and 9 μM (Δ) N-allylsecoboldine.
Figure 12A:
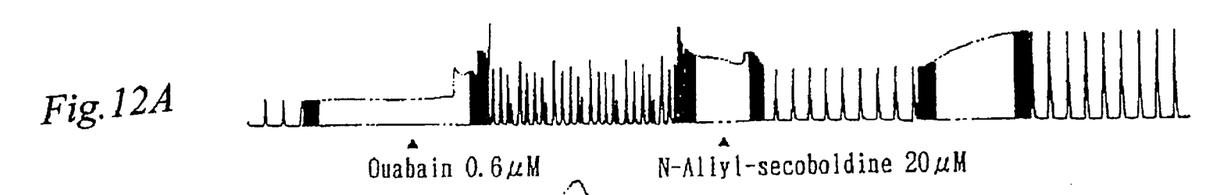
FIG. 12A shows the arrhythmia induced by Ouabain and conversion to normal paced rhythm by N-allylsecoboldine.
Figure 12B:
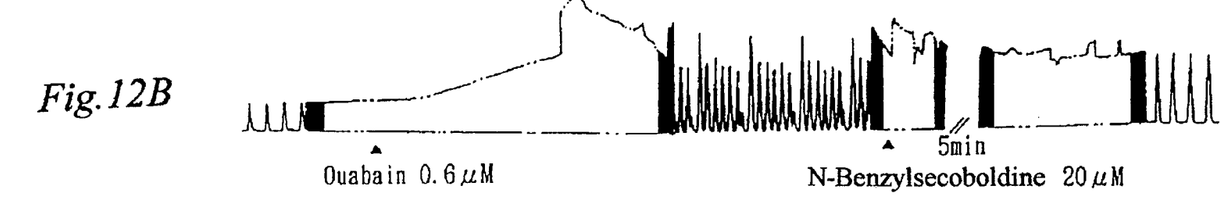
FIG. 12B shows the arrhythmia induced by Ouabain and conversion to normal paced rhythm by N-benzylsecoboldine.
Figure 12C:
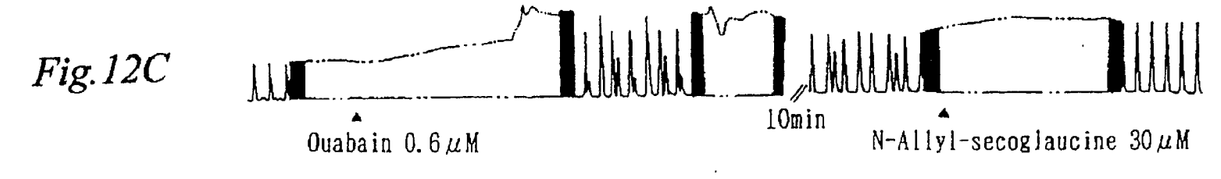
FIG. 12C shows the arrhythmia induced by Ouabain and conversion to normal paced rhythm by N-allylsecoglaucine.
Figures 12D, 12E:
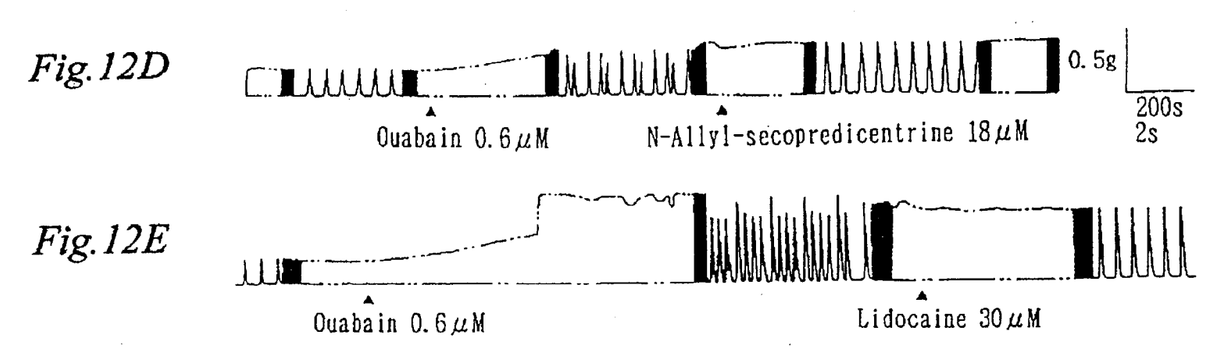
FIG. 12D shows the arrhythmia induced by Ouabain and conversion to normal paced rhythm by N-allylsecopredicentrine.
FIG. 12E shows the arrhythmia induced by Ouabain and conversion to normal paced rhythm by Lidocaine.

Furthermore, the compounds delayed the recovery of inactivated sodium channel, the $t_{1/2}$ for the recovery was prolonged from 50 to 100 ms—see FIG. 9. N-allylsecoboldine shifted the potential-dependent steady state inactivation curve of sodium current to the left, $V_{1/2}$ changed from −60.9 mV to −70.8 mV at 3 μM, and from −60.9 mV to −85.9 mV at 9 μM as illustrated in FIG. 10E. These results indicated that N-allylsecoboldine at higher concentration increased the ratio of inactivated sodium channel, in addition to direct inhibition of this current. Effects on calcium current 3 μM of N-allylsecoboldine (compound 1) did not show any inhibitory effect on calcium current, whereas 12 μM, added in cumulative manner of this compound decreased the calcium current ($I_{Ca}$) of rat ventricle cell to 71% of control. We observed that the calcium current of a non-treated cell retained only 79% of its initial value at 6 minutes after the start of the experiment. Therefore, the actual degree of inhibition in calcium current induced by N-allylsecoboldine was only 9% when this spontaneous rundown in calcium current was taken into consideration (shown in FIG. 11).

THE INHIBITION EFFECTS OF SECOAPORPHINE DERIVATIVES ON THE OUABAIN INDUCED ARRHYTHMIA IN GUINEA PIGS ATRIA

Method:

The left atrium of guinea pigs was first treated with 0.6 μM of ouabain and the contractile force was monitored. Five to 20 minutes later the effects of secoaporphine derivatives at 15 to 30 μM on arrhythmia induced by ouabain were tested and compared with the effect of lidocaine.

Results:

The contractile force of guinea pigs atrium gradually increased after treatment with 0.6 μM of ouabain. Atrial arrhythmia, however, appeared after 5 to 20 minutes. This ouabain-induced arrhythmia was suppressed by treating the guinea pig atrium with 15 to 20 μM N-allylsecoboldine or N-benzylsecoboldine (compound 5), or 30 μM N-allylsecopredicentrine. Nevertheless, the inotropic effect of ouabain on guinea pigs atrial cell still remained. Treatment with 20 μM of N-allylsecoboldine not only inhibited the ouabain-induced arrhythmia but also strengthened the contractile force of guinea pig atrium to 4 to 6 fold before treatment. The ouabain-induced arrhythmia was antagonized only by lidocaine at the concentration of 30 μM or higher, and the contractile force of atrium was strengthened only 2 fold (shown in FIG. 12).

The pharmaceutical preparations according to the invention which contain compounds of the formula I or pharmaceutical acceptable salts thereof are those for oral or parenteral administration which contain the pharmaceutical active ingredient by itself or together with a pharmaceutically acceptable carrier material. Suitable carriers for the oral dosage form are, in particular, fillers, such as sugars, for example lactose, sucrose, mannitol, and additionally binders, such as starch mucilage using, for example wheat, rice or potato starch, and/or, if desired, disintegrating agents or adjuncts. The carriers for parenteral dosage form are, in particular, aqueous solutions and furthermore lipophilic solvents or vehicles, such as fatty oils, and/or, if desired, viscosity-increasing substances, for example sodium carboxymethylcellulose or sorbitol. The preferred dosage is 50 to 300 mg for oral administration and 2 to 15 mg for intravenous administration and can be administered up to 3 times daily.

EXAMPLE 1

N-Allylsecoboldine 1 g of boldine was dissolved in 30 ml of N,N-dimethylformamide(DMF), the mixture was reacted with 1.2 ml of allyl bromide at 100°–110° C. for 2 hours. The residue obtained after evaporation under reduced pressure was purified to give the pure compound (1) N-allylsecoboldine.

UV $\lambda_{max}$ (EtOH, log ε): 356(3.11), 339(3.28), 311(4.15), 299(4.12), 278(4.49), 256(4.88) nm.

IR $\nu_{max}$ (KBr): 3425, 2950, 2825, 1660, 1510, 1460, 1439, 1419, 1275, 1220, 1159, 1100, 1091, 995, 880, 785 cm$^{-1}$.

$^1$H-NMR (CDCl$_3$): δ 8.93(s, H-5), 7.73(d, J=6.6 Hz, H-14), 7.45(d, J=9.1 Hz, H-9), 7.28(s, H-8), 7.13(s, H-2), 5.93(ddt, J=17.0,10.2,6.6 Hz, H-15), 5.21(br d, J=17.0 Hz, Hz-16), 5.17(br d, J=10.2 Hz, HE-16), 4.05(s, 6-OMe), 3.82(s, 4-OMe), 3.23(m, 2H, H-11), 3.16(br d, J=6.6 Hz, H-14), 2.41(s, 13-Me), 2.75(m, 2H, H-12).

EIMS (70 eV)m/z (rel. int.) {M$^+$}: 367(calcd for C$_{22}$H$_{25}$NO$_4$(2), 283(1), 84(100).

EXAMPLE 2

N-benzylsecoboldine 1 g of boldine was dissolved in 30 ml of (DMF), the mixture was reacted with 1.2 ml of benzyl chloride at 100°–110° C. for 2 hrs. The residue obtained after evaporation under reduced pressure was purified to give the pure compound (5) N-benzylsecoboldine.

UV $\lambda_{max}$ (EtOH, log ε): 357(2.98), 339(3.15), 311(3.99), 299(3.96), 278(4.39), 257(4.72) nm.

IR $\nu_{max}$ (KBr): 3380, 2925, 1590, 1505, 1470, 1455 1430, 1410, 1260, 1220, 1150, 1080, 990, 870, 775, 690 cm$^{-1}$.

$^1$H-NMR (CDCl$_3$): δ 8.92(s, H-5), 7.66(d, J=9.1 Hz, H-10), 7.42(d, J=9.1 Hz, H-9), 7.28(s, H-8), 7.27(m, 5H, Ph-H), 7.12(s, H-2), 4.05(s, 6-OMe), 3.82(s, 4-OMe), 3.63(s, H-14), 3.24(m, 2H,H-11), 277(m, 2H,H-12), 2.39(s, 13-Me).

EIMS (70 eV) m/z (rel. int) {M$^+$}: 417(calcd for C$_{26}$H$_{27}$NO$_4$) (6), 283(10), 134(100), 91(56).

EXAMPLE 3

N-allylsecopredicentrine

Compound(1) N-Allylsecoboldine in methanol was reacted with CH$_2$N$_2$ (diazomethane) at 4° C. for 24 hours. The residue obtained after removal of solvent was purified on a silica gel column to give the pure compound(3) N-allylsecopredicentrine. The yield was 16%.

UV $\lambda_{max}$ (EtOH, log ε): 356(2.98), 339(3.12), 311(3.98), 299(3.95), 277(4.26), 255(4.68) nm.

IR $\nu_{max}$ (KBr): 3420, 2960, 2850, 1590, 1510, 1470, 1410, 1360, 1325, 1260, 1220, 1150, 1090, 1035, 995, 885, 840, 810 cm$^{-1}$.

$^1$H-NMR (CDCl$_3$): δ 8.93(s, H-5), 7.78(d, J=9.1 Hz, H-10), 7.53(d, J=9.1 Hz, H-9), 7.18(s, H-2), 7.18(s, H-8), 6.01(dd t, J=16.0,11.7,7.2 Hz, H-15), 5.35(br d, J=11.7 Hz, HE-16), 5.34(br d, J=16.0 Hz, Hz-16), 4.04(s, 6-OMe), 4.02(s, 7-OMe), 3.82(s, 4-OMe), 3.44(m, 2H, H-11), 3.40(br d, J=7.2 Hz, H-14), 2.98(m, 2H, H-12), 2.59(s, 13-Me),

EIMS (70 eV) m/z (rel. int) {M$^+$}: 381(calcd for C$_{23}$H$_{27}$NO$_4$) (1), 297(0.5), 84(100), 41(25).

The following compounds were prepared in a manner analogous to that described as above. Compound(1) N-Allylsecoboldine was reacted with an excess of diazomethane to give compound(4) N-allylsecoglaucine in a 72% yield.

UV $\lambda_{max}$ (EtOH, log ε): 355(3.10), 339(3.25), 313(4.03), 302(4.03) 278(4.28), 257(4.79) nm.

IR $\nu_{max}$ (KBr): 2960, 1600, 1510, 1470, 1420, 1110, 1085, 1035, 990, 890 cm$^{-1}$.

$^1$H-NMR (CDCl$_3$): δ 9.25(s, H-5), 7.72(d, J=9.1 Hz, H-10), 7.50(d, J=9.1 Hz, H-9), 7.18(s, H-8), 7.16(s, H-2), 5.92(dd t, J=17.0,10.2,6.6 Hz, H-15), 5.21(br d, J=17.0 Hz, Hz-16), 5.17(br d, J=10.2 Hz, HE-16), 4.05(s, 6-OMe 4.01(s, 7-OMe), 4.01(5, 3-OMe), 3.90(5, 4-OMe), 3.26(m, 2H, H-11), 3.14(br d, J=6.6 Hz, H-14), 2.75(m, 2H, H-12), 2.40(s, 13-Me).

EIMS (70 eV) m/z (rel. int) {M$^+$}: 395(calcd for C$_{24}$H$_{29}$NO$_4$) (7), 311(3), 84(100), 41(93).

EXAMPLE 4

N-benzylsecopredicentrine

Compound(5) N-benzylsecoboldine in methanol was reacted with equimolar amounts of CH$_2$N$_2$ diazomethane at 4° C. for 24 hours. After removal from silica gel column, the pure compound (6) N-benzylsecopredicentrine was obtained in a yield of 45%.

UV $\lambda_{max}$ (EtOH, log ε): 356(3.15), 339(3.29), 311(3.99), 299(3.99), 278(4.31), 256(4.74) nm.

IR $\nu_{max}$ (KBr): 3425, 2930, 1600, 1510, 1470, 1455, 1430, 1410, 1265, 1230, 1150, 1080, 990, 740, 700 cm$^{-1}$.

$^1$H-NMR (CDCl$_3$): δ 8.93(s, H-5), 7.68(d, J=9.1 Hz, H-10), 7.46(d, J=9.1 Hz, H-9), 7.27(m, 5H, Ph-H), 7.18(s, H-8), 7.14(s, H-2), 4.05(s, 6-OMe), 4.03(7-OMe), 3.82(s, 4-OMe), 3.66(s, H-14), 3.26(m, 2H,H-11), 2.79(m, 2H, H-12), 2.40(s, 13-Me).

EIMS (70 eV) m/z (rel. int) {M$^+$}: 431(calcd for C$_{27}$H$_{29}$NO$_4$) (1), 297(1), 134(100), 91(82).

The following compounds were prepared in a manner analogous to that described as above. Hence compound(5) N-benzylsecoboldine was reacted with equimolar amounts of $CH_2N_2$ diazomethane to give the pure compound (7) N-benzylsecoglaucine (29% yield).

UV $\lambda_{max}$ (EtOH, log ε): 355(2.76), 339(2.90), 313(3.65), 302(3.65), 277(3.92), 257(4.39) nm.

IR $v_{max}$ (KBr): 3000, 2925, 1610, 1595, 1500, 1470, 1460, 1440, 1415, 1360, 1270, 1258, 1230, 1189, 1150, 1100, 1080, 990, 845, 760, 715, 685 $cm^{-1}$.

$^1$H-NMR (CDCl$_3$): δ 9.25(s, H-5), 7.66(d, J=9.1 Hz, H-10), 7.47(d, J=9.1 Hz, H-9), 7.27(m, 5H, Ph-H), 7.18(s, H-8), 7.15(s, H-2), 4.05(s, 6-OMe), 4.02(7-OMe), 4.00(s, 3-OMe), 3.90(s, 4-OMe), 3.65(s, H-14), 3.30(m, 2H, H-11), 2.80(m,2H, H-12), 2.40(s, 13-Me).

EIMS (70 eV) m/z (rel. int) {M$^+$}: 445(calcd for $C_{28}H_{31}NO_4$) (1), 311(1), 134(100), 91(76).

EXAMPLE 5

| Active compound | 50.0 mg |
| Lactose | 60.0 mg |
| Starch | 9.0 mg |
| Avicel | 30.6 mg |
| Magnesium Stearate | 0.4 mg. |

We claim:

1. A compound of formula I wherein each of $R_1$ and $R_2$ is H or $CH_3$; $R_3$ is allyl, or propyl, $R_4$ is methyl and a pharmaceutically acceptable salt thereof.

2. A compound according to claim 1 which is a member selected from the group consisting of N-allylsecoboldine, N-allylsecopredicentrine and N-allylsecoglaucine.

3. A pharmaceutical composition for oral administration for the treatment of arrhythmia in unit dosage form comprising 50–300 mgs. per dose of a compound of formula I according to claim 1.

4. A pharmaceutical composition for parenteral administration for the treatment of arrhythmia in unit dosage form comprising 2–15 mgs. per dose of a compound of formula I according to claim 1.

5. A method of treating a living subject affected by arrhythmia which consists of administering to said subject an effective amount of a secoaporphine compound having the formula II, wherein each of $R_1$ and $R_2$ is H or $CH_3$; $R_3$ is methyl, allyl, benzyl, ethyl or propyl, $R_4$ is methyl and a pharmaceutically acceptable salt thereof.

6. The method according to claim 5 wherein formula II compound is a member selected from the group consisting of N-allylsecoboldine, N-allylsecopredicentrine, N-allylsecoglaucine, N-benzylsecoboldine, N-benzylsecopredicentrine, N-benzylsecoglaucine, N-methylsecoglaucine, and N-methylsecropredicentrine.

* * * * *